(12) United States Patent
Schneider et al.

(10) Patent No.: US 10,331,996 B2
(45) Date of Patent: Jun. 25, 2019

(54) INJECTOR WITH ELECTRICAL CIRCUIT DESTRUCTIBLE DUE TO USE

(71) Applicant: TECPHARMA LICENSING AG, Burgdorf (CH)

(72) Inventors: Andreas Schneider, Bern (CH); Leos Urbanek, Bern (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 15/944,646

(22) Filed: Apr. 3, 2018

(65) Prior Publication Data

US 2018/0225560 A1 Aug. 9, 2018

Related U.S. Application Data

(63) Continuation of application No. PCT/CH2016/000109, filed on Aug. 18, 2016.

(30) Foreign Application Priority Data

Oct. 7, 2015 (CH) ...................................... 1458/15

(51) Int. Cl.
*A61M 5/20* (2006.01)
*A61M 5/32* (2006.01)
(Continued)

(52) U.S. Cl.
CPC ..... *G06K 19/07773* (2013.01); *A61M 5/2033* (2013.01); *A61M 5/3202* (2013.01);
(Continued)

(58) Field of Classification Search
None
See application file for complete search history.

(56) References Cited

U.S. PATENT DOCUMENTS

| 3,126,004 A | 3/1964 | Sarnoff |
| 2006/0152364 A1 | 7/2006 | Walton |
| 2012/0280815 A1 | 11/2012 | Edwards et al. |

FOREIGN PATENT DOCUMENTS

| DE | 102012112297 A1 * | 6/2014 | ............. B65D 55/06 |
| WO | 2006102678 A1 | 9/2006 | |

(Continued)

OTHER PUBLICATIONS

International PCT Search Report dated Mar. 13, 2017, for Application No. PCT/CH2019/000109, 6 pages.

(Continued)

*Primary Examiner* — Kristy A Haupt
(74) *Attorney, Agent, or Firm* — Dorsey & Whitney LLP

(57) ABSTRACT

The invention relates to a device for administering a medicament, comprising a first appliance part; at least a second appliance part, which can be moved from a first state to at least a second state relative to the first appliance part before, during or after administration; an activatable identification element having a carrier; a RFID circuit with an antenna port and at least one signal terminal; at least one sensor which comprises at least two operatively linked sensor elements; at least one sensor element being connected to the at least one signal terminal, as well as an antenna which is connected to the antenna port. According to the invention, the carrier receives or connects the RFID circuit, the antenna and the at least one sensor element, wherein at least a region or section of the carrier is connected at least to the first appliance part.

19 Claims, 8 Drawing Sheets

(51) Int. Cl.
    *A61M 5/50*          (2006.01)
    *G06K 7/10*          (2006.01)
    *G09F 3/03*          (2006.01)
    *G06F 16/951*        (2019.01)
    *G06F 16/955*        (2019.01)
    *G06K 19/077*       (2006.01)

(52) U.S. Cl.
    CPC ......... *A61M 5/5086* (2013.01); *G06F 16/951* (2019.01); *G06F 16/955* (2019.01); *G06K 7/10366* (2013.01); *G06K 19/07798* (2013.01); *A61M 2005/2013* (2013.01); *A61M 2205/273* (2013.01); *A61M 2205/60* (2013.01); *G09F 3/0335* (2013.01)

(56) References Cited

FOREIGN PATENT DOCUMENTS

| | | | |
|---|---|---|---|
| WO | 2009140782 | A1 | 11/2009 |
| WO | 2013160152 | A1 | 10/2013 |
| WO | 2014183226 | A1 | 11/2014 |
| WO | 2015071354 | A1 | 5/2015 |

OTHER PUBLICATIONS

International Preliminary Report on Patentability dated Apr. 19, 2018 for Application No. PCT/CH2016/000109, 10 pages.

\* cited by examiner

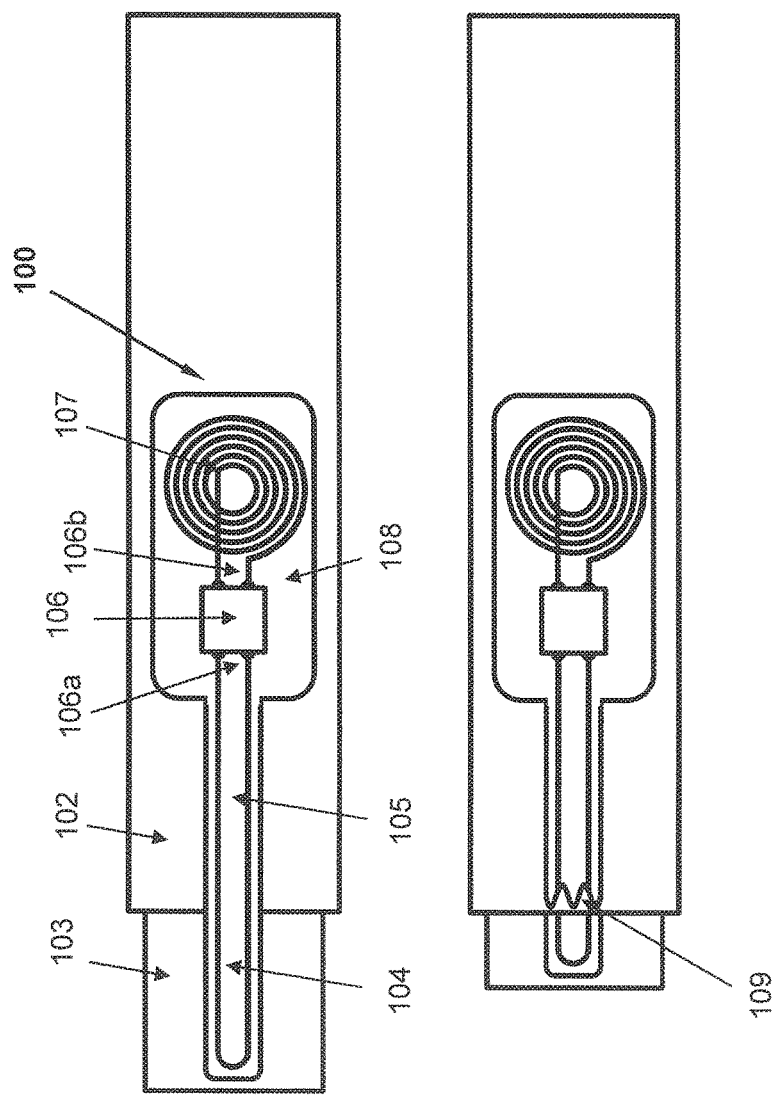

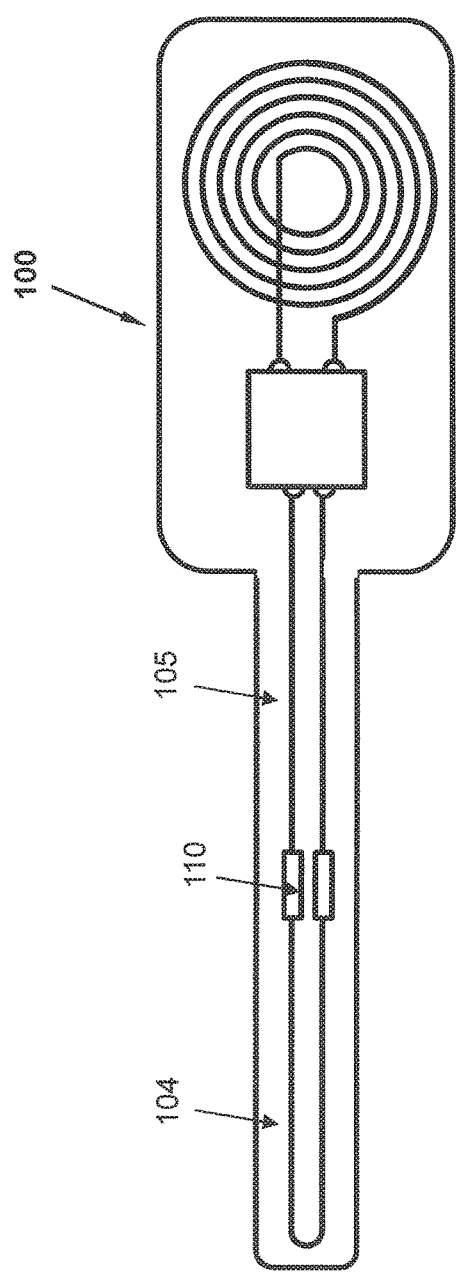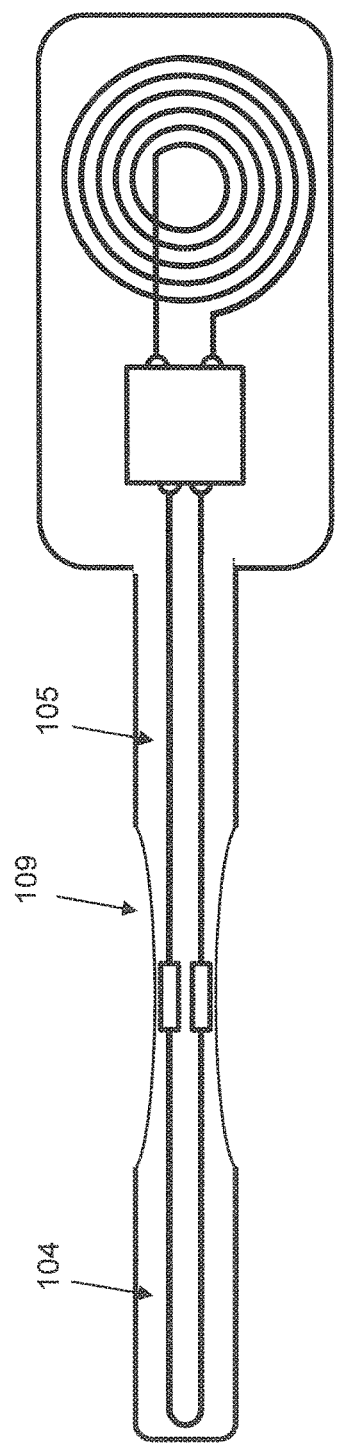
Fig. 4a
Fig. 4b

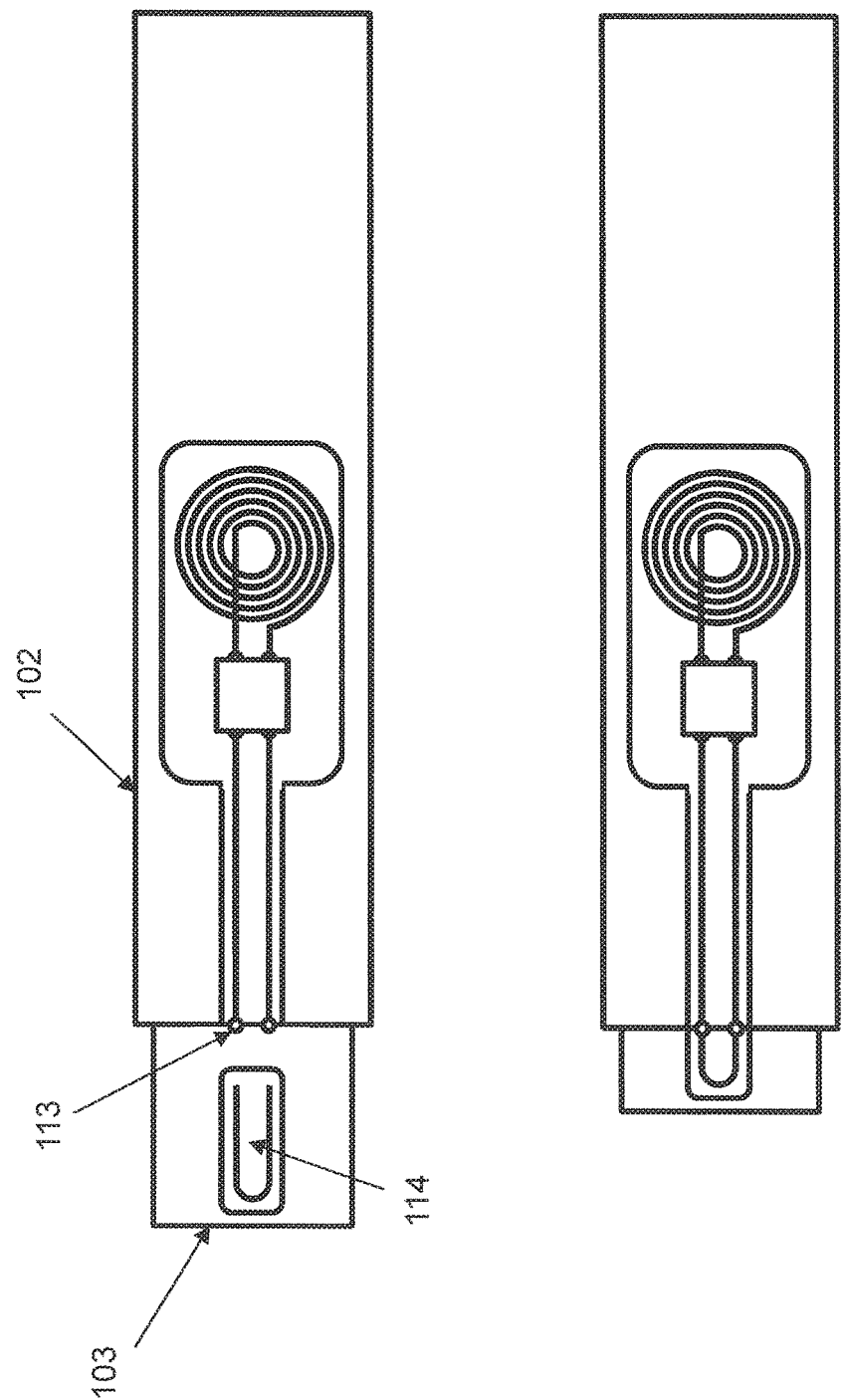

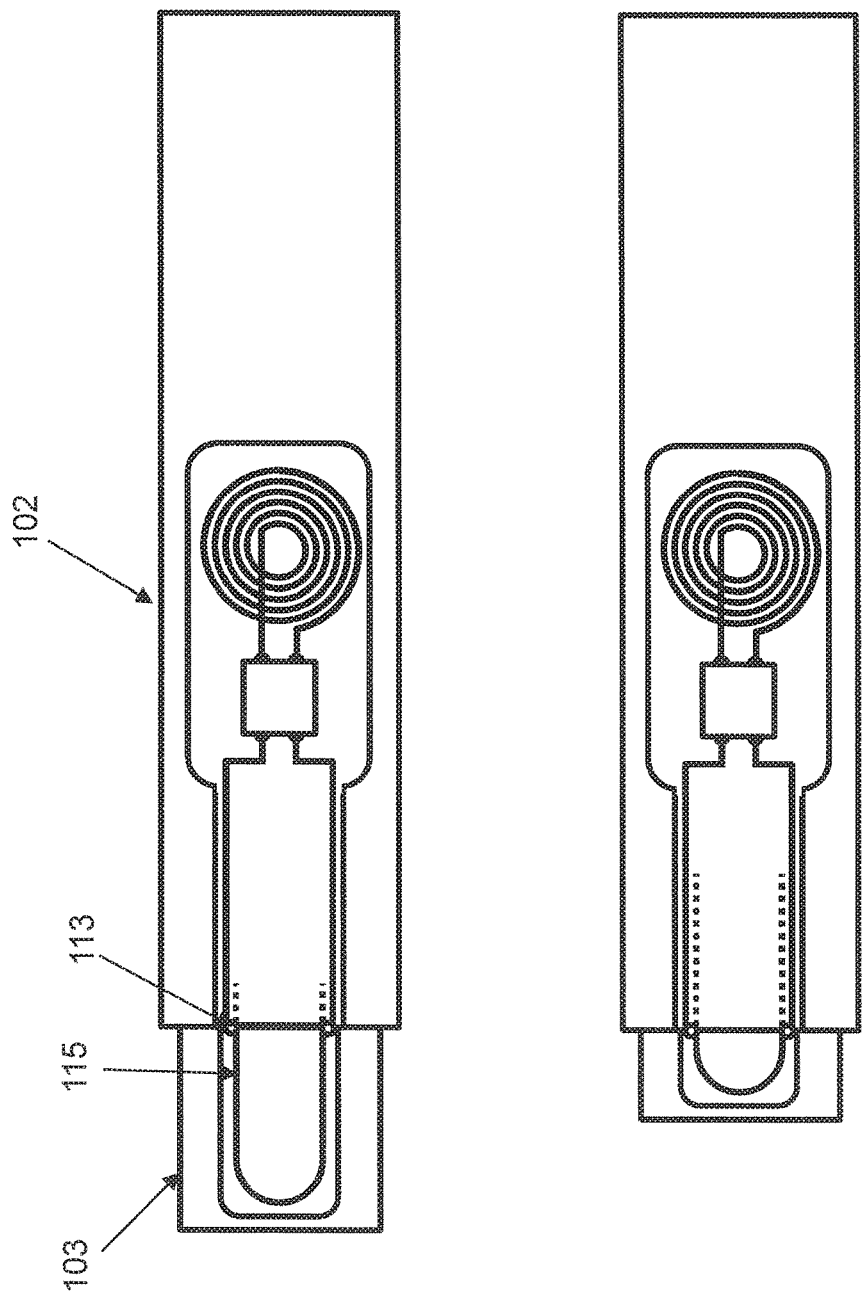

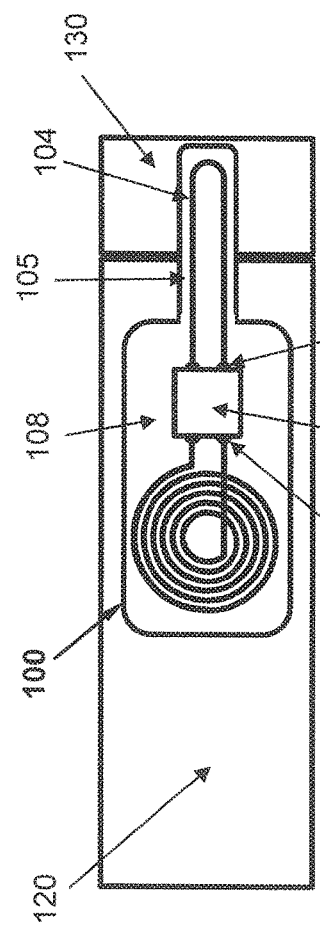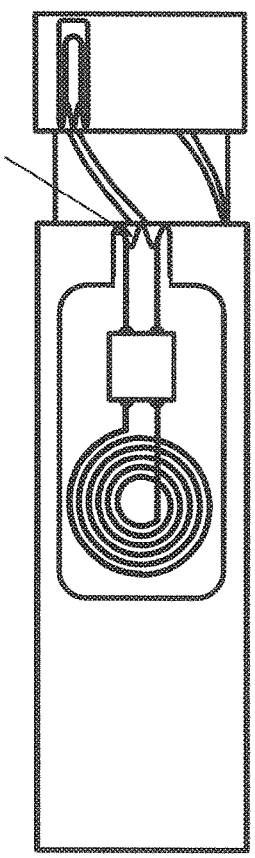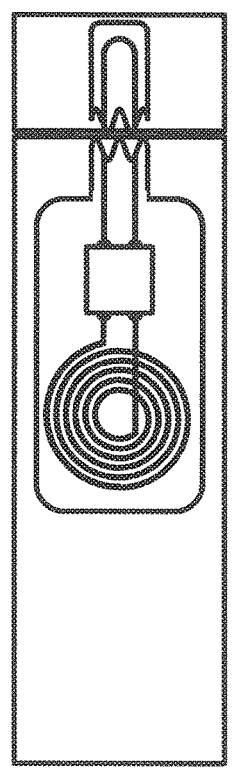
Fig. 8a
Fig. 8b
Fig. 8c

INJECTOR WITH ELECTRICAL CIRCUIT DESTRUCTIBLE DUE TO USE

CROSS-REFERENCE TO RELATED APPLICATIONS

This application is a continuation of International Application No. PCT/CH2016/00109 filed Oct. 4, 2016, which claims priority to Swiss Application No. 01458/15 filed Oct. 7, 2015, the entire contents of all of which are incorporated by reference herein in their entirety.

FIELD OF THE INVENTION

The invention relates in general to devices and methods for parenteral administration of medicines. Examples are administration devices such as insulin pumps, patch pumps, bolus injectors, automatic injectors, pen injectors, auto pens, but also conventional syringes and prefilled syringes. In the clinical environment and especially in self-medication, clearly defined remaining product and device status messages to patients or care personnel are advantageous for guaranteeing a safe and effective use. With administration equipment currently available on the market, the patient infers the usage state of the device based on visual, acoustic, haptic or tactile signals. Visual signals can be recognizable, for example, on the basis of their change of shape or color, acoustic signals by a clicking noise, haptic or tactile signals with a tangible change of shape, or due to mechanical accelerations. Such signals, however, are often transient and can be ignored, not heard or forgotten. Additional and novel feedbacks and confirmations, particularly regarding the usage status and the successful conclusion of an administration, can decisively contribute to the improvement of patient safety, patient trust and therapy compliance. Furthermore, such feedbacks and status messages can preferably also be recorded and evaluated immediately or shifted in time or compared to specifications. The invention additionally improves guarantee of therapy by the care provider and enables monitoring by the service provider, including economic aspects.

BACKGROUND

The PCT application with international publication number WO2006/102678 A1 presents an invention that provides "tamper-evident" safety packages by means of RFID tags. The invention relates to containers and claims the secure recognition of a previously performed first opening of the container. Detecting and signaling specific usage conditions of an administration device for medicines is not taught.

The PCT application with international publication number WO2009/140782 A1 presents an invention that provides cartridges having a pressure-measuring device and a transmission device. The invention teaches and claims cartridges having pressure-monitoring devices for continuous administration of fluids. Detecting and signaling specific usage conditions of administration devices for medicines is not taught.

The invention from the PCT application with international publication number WO2013/160152 A1 relates to an insert for a medicine that contains a data memory device and a syringe. An integral carrier means that receives and connects this data storage device together with the antenna and the sensor is not taught or disclosed.

The invention from the PCT application with international publication number WO2015/071354 A1 relates to an administration device that provides a time parameter autonomously and can cause it to be displayed. An energy source is constantly necessary for this and is also claimed, together with the disclosed time display. A passive device and corresponding methods for detecting and signaling specific usage states of an administration device for medicines without constant energy supply is not taught.

SUMMARY OF THE INVENTION

A problem addressed by the present invention is that of providing devices and methods that fulfill the detection and signaling of different usage conditions of an administration device more specifically or simply or securely than the teachings of the prior art. A problem addressed by the present invention is that of improving a desired therapy and making it more economical.

The invention can be described as follows according to one of its aspects: An administration device is furnished with an activatable identifying element. Preferably in the form of a printable element that contains an electronic circuit of the type known as an RFID circuit. The electronic circuit is temporarily supplied with energy by a read-out device wirelessly via an antenna structure and is thereby capable of transmitting information regarding the current usage condition of the administration device to the read-out device. Embodiments and methods according to the invention follow from the independent claims and advantageous improvements and application cases of the invention from the dependent claims, the description and the figures.

GENERAL DESCRIPTION

The administration devices. The invention proceeds from an administration device for parenteral administration of a product, in particular a medicine. For example, the administration device can be an autoinjector or bolus injector which can contain in particular the following elements, which are formed from one or more device parts:

a. a housing, which is preferably shell-shaped and formed longitudinally with a longitudinal axis and has a protective cover that can be removed from the distal end, b. a product container, in particular a syringe, at the distal end of which a needle or cannula is arranged, more particularly detachably or non-detachably, which container contains a piston that is preferably sealingly and displaceably arranged on the wall of the product container surrounding it and is retained in a product container holder, which can also be called a syringe, wherein the product container holder is connected axially fixedly to the housing, preferably permanently, in particular snap-fit or form-fittingly connected thereto, or can be displaced in the distal direction relative to the housing by means of the force of a drive means or driver, in particular a compression or a motive spring, wherein the needle is moved or projects or protrudes out of the housing beyond the distal end of the housing, and is covered with a needle sleeve before use.

c. a needle protection sleeve, which has in particular the function of a needle protection sleeve and a triggering device for discharging product, wherein the needle protection sleeve can be moved from an initial position in which the distal end of the needle protection sleeve protrudes distally from the needle tip of the needle, so that access to the needle is prevented, into the housing, more particularly in the proximal direction, in particular against the force of a needle protection sleeve spring, so that the needle protrudes from or is moved from the distal end of the needle protection sleeve, preferably protruding with a length that corresponds approximately to the injection depth of the needle, preferably for a subcutaneous injection,
d. an actuatable button, which in particular acts together with the needle protection sleeve on the triggering device,
e. a plunger and a discharge spring, wherein it is preferred that the discharge spring is a coil spring acting as a compression spring, wherein the plunger is arranged in the housing and by means of the discharge spring, which is in particular preloaded in the delivery condition of the autoinjector and preferably at least partially arranged inside the preferably sleeve-shaped plunger, can be displaced in the distal direction along the longitudinal axis of the autoinjector or the housing when the plunger is released by the trigger device, wherein the displacement of the plunger by means of the force of the discharge spring in the distal direction has the effect that the piston, against which the plunger presses at least during the displacement, is driven by the plunger and displaces the product out of the product container, more particularly via the needle,
f. a blocking device, which prevents the needle protection sleeve from releasing the needle again after a first actuation or completed administration.

The administration device can further comprise a dose-setting element, which preferably forms an outer surface of the administration device and can be gripped by the user of the administration device, wherein the dose-setting element can be rotated and/or displaced relative to the housing, preferably by the user's muscular force, to set a dose to be discharged from the product container, and can assume at least two different positions, specified in particular by catch positions, relative to the housing.

Setting and administering a dose of medication, in particular with the autoinjector or bolus injector, can have the following steps and corresponding relative movements:
a. removing the protective cap or a protection means from the housing with a twisting or pulling movement,
b. removing the needle sleeve from the syringe with a twisting or pulling movement,
c. by moving the dose-setting element, setting a dose to be administered,
d. pressing the button, whereby an administration is unlocked or can be triggered with the triggering device,
e. positioning and pressing the needle protection sleeve and/or the housing onto an injection point, whereby the needle protection sleeve is moved into the housing and can unlock or trigger an administration,
f. piercing the needle into the injection point by a longitudinal movement of the syringe relative to the needle protection sleeve and/or the housing,
g. administering the medicine, wherein the drive spring is decompressed and displaces the plunger in a longitudinal movement relative to the parts fixed to the housing, in particular relative to the syringe, whereby the plunger pushes, with the distal end or flange thereof, the piston into the carpule, whereby the medicine is pressed through the cannula of the needle,
h. —removing the needle protection sleeve from the injection point, whereby the needle protection sleeve is moved out of the housing by the force of the needle protection sleeve spring until the distal end of the needle protection sleeve protrudes distally past the needle tip of the needle and the blocking device is latched by the recoil movement of the needle protection sleeve against the housing,
i. placing the protective cap or the protective means on the housing.

For example, the administration device can be an autoinjector or bolus injector, which can contain in particular the following elements, which are formed from one or more device parts:
a. a housing, which is preferably shell-shaped and formed longitudinally with a longitudinal axis and has a protective cover that can be removed from the distal end,
b. a carpule holder that can be connected to the housing and receives a carpule that encloses a medicine, wherein the carpule has a displaceable piston and a septum through which a cannula can be pierced, which conducts the medicine to the administration point, wherein the cannula can be connected as a needle to the carpule,
c. a piston rod having a flange that bears against the piston. The piston rod is furnished with a thread and a longitudinal guide groove, wherein the thread is engaged with an output drive sleeve and the longitudinal guide groove with the housing, or alternatively the thread is engaged with the housing and the longitudinal guide groove with the output drive sleeve,
d. a coupling sleeve, which is coupled axially displaceably to the output drive sleeve and can be connected via a coupling to a drive sleeve, wherein the coupling can be actuated by a button,
e. the drive sleeve is furnished with a thread that remains engaged with the housing, whereby the drive sleeve can be screwed in and out along the longitudinal axis relative to the housing, or the drive sleeve can be moved against or with the force of a motive spring, in particular rotating relative to the housing.

Setting and administering a dose of medication, in particular with the injection pen or autopen, can have the following steps and corresponding relative movements:
f. removing the protective cap from the housing with a twisting or pulling movement,
g. connecting a needle to the carpule holder with a twisting or compressive movement,
h. by screwing the drive sleeve in the housing with the button not pressed, setting a dose to be administered,
i. preparing the administration of the set dose by pressing the button, wherein the drive sleeve is coupled to the coupling sleeve,
j. administering the medicine by screwing in or pressing in the drive sleeve or rotating it by means of the motive spring with the button pressed, whereby the coupling sleeve is co-rotated, which drives the output drive sleeve rotationally, which, via the engagement with the piston rod and its engagement with the housing, sets the piston rod into a longitudinal movement, whereby the flange displaces the piston in the carpule, whereby medicine is pressed through the cannula,
k. placing the protective cap on the housing.

The activatable identifying means or element. According to the invention, the activatable identifying means or element comprises a carrier or carrier element or means, an RFID circuit having an antenna terminal and at least one signal terminal, at least one pickup that is connected to the at least one signal terminal, and an antenna that is connected to the antenna terminal, wherein the carrier receives and/or connects the RFID circuit, the antenna and the at least one pickup. The carrier can thus be a substantially two-dimensional or three-dimensional structure, and is thus preferably constructed as a flexible circuit board, a film or as a 3D-MID "molded interconnected device" assembly. Particularly on the flat outer sides, the activatable identifying means or element or the carrier can have at least one imprint or optically readable code as is known from conventional labels. At least one outer side of the activatable identifying element can also be used, by means of a suitable adhesive or based on lockable, more particularly formfitting structures, to fixedly or operatively connect the activatable identifying element to parts of the administration device.

The read-out devices. According to the invention, a read-out device—as is well known from the prior art—allows the reading of at least two different codes from the RFID circuit. The read-out device thus supplies the activatable identifying element temporarily with energy, decodes the read information and displays it directly or by an app, stores the information for example, and/or links the information to a time or date stamp and/or transmits corresponding information to higher-level systems such as a workstation, a host computer, a network node or to network-attached storage, in particular cloud storage.

The RFID circuit, if it is supplied externally with energy, captures at least one signal from the pickup and codes and transmits it to a read-out device. A suitable antenna allows electromagnetic or inductive coupling to the read-out device, whereby energy and information can be transmitted. Different technical solutions and transmission protocols, such as "near-field communication (NFC)," which has been elevated to a standard to some extent, are known from the prior art.

The pickups and their signals. Passive or active sensors can be used as pickups. Passive sensors are, in particular: switching contacts, disconnectable conductors or conductor loops, resistive strain gauges, variable resistors, capacitors or potentiometers, galvanically or capacitively scannable conductor structures for binary codes, in particular Gray codes, reed contacts, resonant circuits and Wiegand sensors. Active sensors are, in particular: photoelements, phototransistors, Hall elements, magnetoresistive elements, piezo elements, inductive and capacitive sensing devices, thermoelements, integrated circuits, measuring transducers. Active sensors are often constructed in two parts and contain amplifiers, wherein a transmitter or field transmitter or field influencer cooperates as a transmitter with a corresponding receiver or detector. The signals are accordingly represented as at least on/off switching states or as analog values, e.g. resistance, voltage or amperage.

Usage states, codes and information. The above-mentioned signals are assigned to a specific usage state and represented in an administration device according to the invention as at least two distinguishable relative positions of one or more device parts that form the administration device. Absolute positions such as the position in a gravitational field or in an external magnetic field or electromagnetic field or the accelerations of inertial masses can also be the basis of signals. The signals are processed in the RFID circuit as codes that characterize these usage states. Immediately when read, or offset in time or space, these codes are used for transmitting information and/or for synthesizing more complex messages, which can be output or stored for a user.

Application cases and methods according to the invention can have the following steps:
 a. reading a first code from the RFID circuit if at least one device part is in a first state or position,
 b. reading a second code distinguishable from the first code from the RFID circuit if at least one device part is in a second state or position,
 c. outputting messages depending on the read code, particularly as a text or image on a display or as a video or audio message or an URL,
 d. linking the codes or messages to a time stamp,
 e. storing the codes or messages in the read-out device or a network-attached storage site, a database or cloud storage,
 f. comparing the codes or messages to specified values and outputting corresponding confirmations or warnings,
 g. transmitting the codes or messages to a host system or a network or a database or a remote control unit or a blood sugar measuring device or a telemedicine system,
 h. querying databases and outputting corresponding responses.

Systems and interfaces. A first system can be formed from an administration device having activatable identifying element, wherein a first interface provides the operating functions for the user or medical personnel, or logistical functions in production or a pharmacy, directly at the administration device. Examples of these functions can be: removing a protection device, triggering the injection, securely locking after use.

A second system is formed according to the invention by adding at least one read-out device to the first system, wherein a second interface provides the above-described RFID transmission and a third interface provides the operating functions on the read-out device for the user or medical personnel, or logistical functions in production or a pharmacy.

A third system is formed by adding at least one network-integrated unit or a host computer to the second system, wherein a fourth interface provides network functions, client/server transactions or cloud services for the user or medical personnel, or logistical functions in production or pharmacy or for payment agencies such as insurance companies.

The term "medicine" or "product" comprises any medical formulation that is suitable for controlled administration by a means such as a cannula or a hollow needle, the term comprising, for example, a liquid, a solution, a gel, a fine suspension or an aerosol that contains one or more medical active substances. "Medicine" can be a composition with a single active substance or a premixed or co-formulated composition with multiple active substances from a single container. Medicine comprises pharmaceuticals such as peptides (e.g. insulin, and insulin-containing medicines, preparations containing GLP-1 and derived or analogous substances), proteins and hormones, biologically obtained or active substances, active substances based on hormones or genes, nutritional formulations, enzymes and additional substances, both in solid (suspended) or liquid form, but also polysaccharides, vaccines, DNA or RNA or oligonucleotides, antibodies or parts of antibodies as well as suitable base, auxiliary and carrier substances.

Aspects of the Invention

An administration device for a medicine, having a first device part (2, 55, 102, 120), at least one second device part (3, 61, 103, 130) that can be moved relative to the first device part from a first condition into at least one second condition before or during or after an administration, and an activatable identifying element (100) having a carrier (108), an RFID circuit (106) with an antenna terminal (106b) and at least one signal terminal (106a), at least one pickup (104, 105) having at least two operatively connected pickup parts (104, 105), of which at least one pickup part (105) is connected to the at least one signal terminal (106a), and an antenna (107) that is connected to the antenna terminal (106b), wherein the carrier (108) receives or connects the RFID circuit (106), the antenna (107) and the at least one pickup part (105), wherein at least one region or portion of the carrier (108) is connected to at least the first device part (2, 55, 102, 120), preferably further comprising, wherein a. the at least one region or portion of the carrier (108) has the at least one pickup part (105), and the second pickup part (104) is connected to the second device part (3, 61, 103, 130), b. the at least one region of the carrier (108) also receives the second pickup part (104) and is connected to the second device part (3, 61, 103, 130) such that a movement of the at least [one] second device part (3, 61, 103, 130) relative to the first device part (2, 55, 102, 120) from the first into the at least [one] second state deforms or separates the at least one region of the carrier mechanically, wherein the deformation or separation (109) of the at least one region of the carrier (108) influences the operative connection of the at least two pickup parts (104, 105) and effects a signal change of the at least one pickup (104, 105), c. the at least one pickup (104, 105) has a separable conductor (104) or a variable resistor (110) or a piezoelectric transducer (110) for changing the signal, d. the operative connection between the at least one pickup part (105) and the second pickup part (104) can be established galvanically or via a magnetic or electrical or electromagnetic field is characterized in that the at least one pickup (104, 105) has respective corresponding contacts (113) and mating contacts (114, 115) or respective corresponding detectors (111) and transmitters (112), e. a movement of the at least [one] second device part (3, 61, 103, 130) relative to the first device part (2, 55, 102, 120) from the first to the at least one second state effects a signal change of the pickup (104, 105, 111, 112, 113, 114, 115), f. the first and the second device parts each comprise one of: housing (2, 55,102,120), protective cap (4, 51), protective means, design shell, grip shell, mechanism holder (5, 56), packaging, sleeve, blister film, needle adapter, needle, hollow cannula, carpule or syringe holder (1, 52), cap (12), needle protection sleeve (3, 103, 130), pull tab (4), carpule (53), septum, syringe, piston, flange (54), piston rod (7, 58), plunger (7), metering sleeve (60), metering ring (61), drive element, drive spring, motive spring, scale element (60), counter (65), locking element (8, 15), drive spring (9), drive motor, ratchet (67), click element (66, 67), catch arm, blocking element (67), holding arm, guide, trigger element (3, 103, 139, 15, 64), trigger (64), coupling (62), button, thread (58), gear unit (58, 65), stop, g. the device is an autoinjector, injection pen, autopen, infusion pump, patch pump, inhaler or bolus injector.

h. the carrier is two-dimensional, can carry readable information, and is applied at least in part to the outer surface of the administration device or to a surface of the administration device that is visible from outside, i. the carrier is attached with a form fit or frictional fit to at least the first device part and at least in part in the interior of the administration device, in particular in an annular gap formed between the device parts, j. the RFID circuit provides codes that can be distinguished by a read-out device, in particular a smartphone, which are a function of the signal that is present at the at least one signal terminal, k. the RFID circuit is compatible with devices and systems that operate according to the near field communication (NFC) protocol.

In addition, a method performed with an administration device according to the invention and at least one read-out device, containing at least one of the following steps:

a. reading a first code from the RFID circuit, if the second device part is in the first state.

b. reading a second code distinguishable from the first code from the RFID circuit if the second device part is in the second state.

additionally containing at least one of the following steps:

c. outputting messages depending on the code read, particularly as a text or image on a display or as a video or audio message or an URL, d. linking the codes or messages to a time stamp, e. storing the codes or messages in the read-out device or a network-attached storage site, a database or cloud storage, f. comparing the codes or messages to specified values and outputting corresponding confirmations or warnings, g. transmitting the codes or messages to a host system or a network or a database or a remote control unit or a blood sugar measuring device or a telemedicine system, h. querying databases and outputting corresponding responses.

BRIEF DESCRIPTION OF THE DRAWINGS

FIGS. 3a-3c show an administration device according to the invention in different usage states.

FIG. 4a-4b show a modification according to the invention of the pickup in a first and a second state.

FIGS. 6a-6b show an additional modification according to the invention of the activatable identifying element in a first and a second state.

FIGS. 7a-7b show an additional modification according to the invention of the activatable identifying element in a first and a second state.

FIGS. 8*a*-8*c* show an additional administration device according to the invention in different usage states.

DETAILED DESCRIPTION

Figure 1:
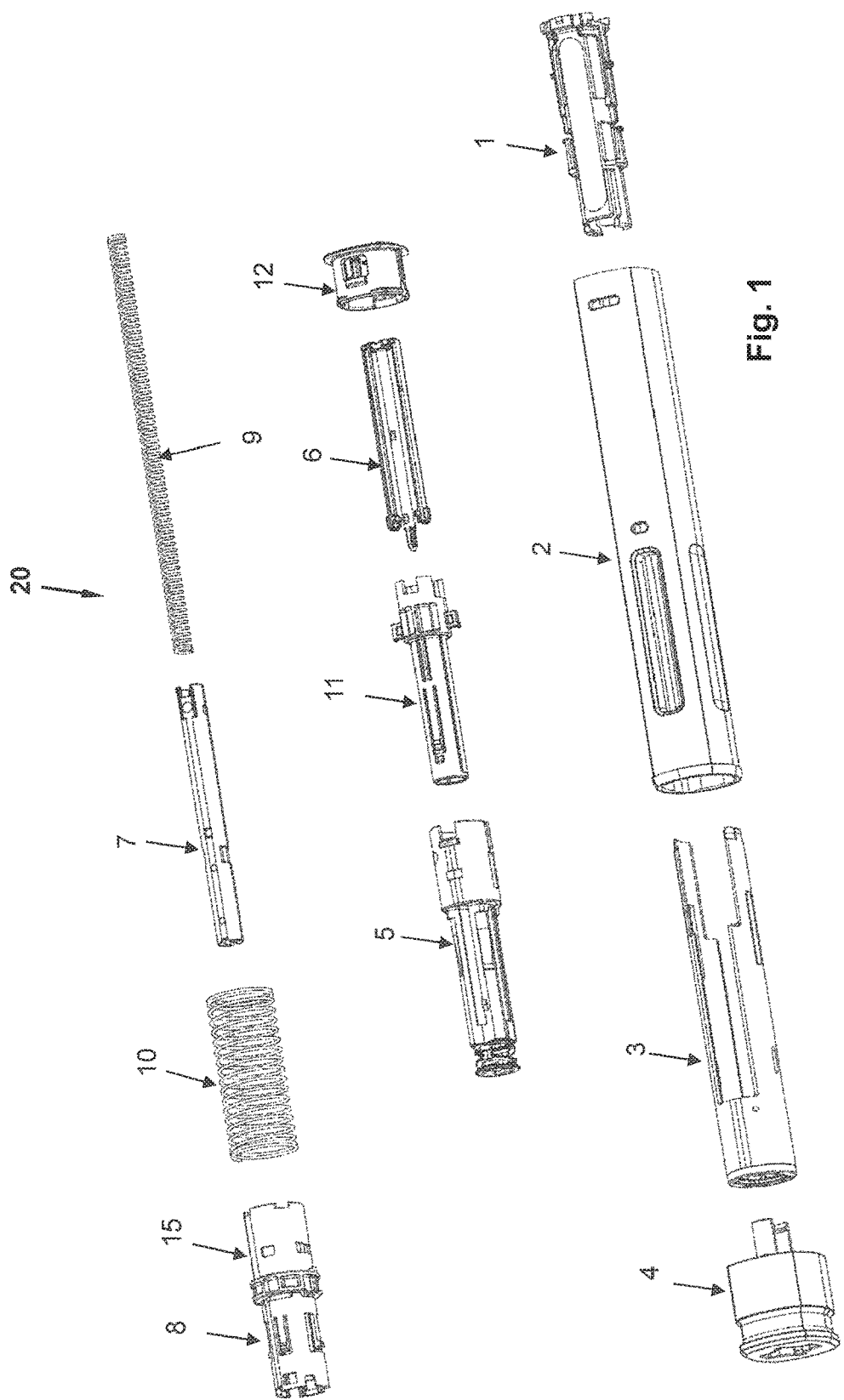
FIG. 1 illustrates, on the example of an autoinjector, the device parts on which the invention can be performed, with an activatable identifying element.

FIG. 1 illustrates, on the example of an autoinjector, the device parts on which the invention can be performed, with an activatable identifying element. In principle, the invention can be performed on all device parts of the autoinjector or of a comparable administration device that can assume differentiable positions and characterize significant states or statuses, in particular before, during or after use. According to the invention, at least two of the individual parts described below can be the respective first and second device part of the autoinjector shown in each case, so long as they move relatively to one another and thereby establish a change of the usage state:

In a first phase, when the autoinjector is being prepared for use by opening, the protective cap 4 and at the same time the needle-covering sleeve (not shown), which are removed from the syringe (not shown), preferably move relative to the housing 2 or parts fixed to the housing, in particular syringe holder 1, the syringe (not shown), end cap 12 and mechanism holder 5. Then the autoinjector can be positioned at and pressed onto the injection point. In this second phase, the needle protection sleeve 3, together with the front blocking sleeve 15 and the rear blocking sleeve 8 and under compression of the needle protection spring 10, preferably moves relative to the above-mentioned parts fixed to the housing and releases the connection between plunger 7 and retaining pin 6. The discharge then follows as the third phase, which is initiated by a proximal displacement of the retaining pin 6 with the rear blocking sleeve 8 and the striking thereof onto the mechanism holder 5. The now-released plunger 7 is displaced axially, driving the click sleeve 11 over a portion of the distance, whereby the needle protection spring 10 is further compressed. This distal displacement of the plunger 7 is effected by the now decompressing discharge spring 9 and results in a distal displacement of the piston (not shown) in the syringe. At the end of this distal displacement of the plunger 7 and the displacement of the medicine effected thereby, the plunger 7 again releases the click sleeve 11, whereby the latter is moved proximally by the force of the needle protection spring and strikes against the end cap 12, which is fixed relative to the housing. In the subsequent fourth phase, the autoinjector is removed from the injection point, and the needle protection sleeve 3, together with the front blocking sleeve 15, is moved distally by the needle protection spring 10. The needle protection sleeve 3 now again covers the needle on the syringe (not shown) and the front blocking sleeve 15 locks together with the rear blocking sleeve 8 such that the "extended telescope" formed thereby reliably prevents another pressing of the needle protection sleeve 3 into the housing.

FIGS. 3*a, b, c* show an administration device according to the invention in different usage states. For the sake of simplicity and as an example, the only parts of the administration device that are shown are the housing 102 as the first device part and the needle protection sleeve 103 as the second device part. Other device parts, particularly those as described above, are also suitable for carrying out the invention if modified.

FIG. 3*a* shows an administration device according to the invention in a first state with an activatable identifying element 100 having the carrier 108, wherein the carrier 108 mechanically accommodates the RFID circuit 106, the antenna 107 and the pickup 104, 105, and connects them electrically to the antenna terminal 106*b* and the signal terminal 106*a*. As shown, one region or portion 105 is operatively connected to the first device part 102 and another region or portion 104 is operatively connected to the second device part 103.

FIG. 3*b* shows the administration device according to the invention in a second state, wherein the integrity of the pickup 104, 105 has been disrupted by the movement of the first device part 102 relative to the second device part 103 and the above-mentioned operative connection has been disrupted, in particular, the illustrated conductor or conductor loop 104 has been permanently interrupted mechanically and electrically at a separation point 109 in the third state, as can be seen in FIG. 3*c*.

FIGS. 4*a* and 4*b* show a modification of the pickup 104, 105 according to the invention in a first and a second state, wherein a reversible or irreversible deformation 109 of the carrier and electrical elements 110 mounted thereon has taken place due to the movement of the first device part 102 relative to the second device part 103, whereby electrical parameters, in particular resistance or impedance values, are changed measurably.

Figure 5:
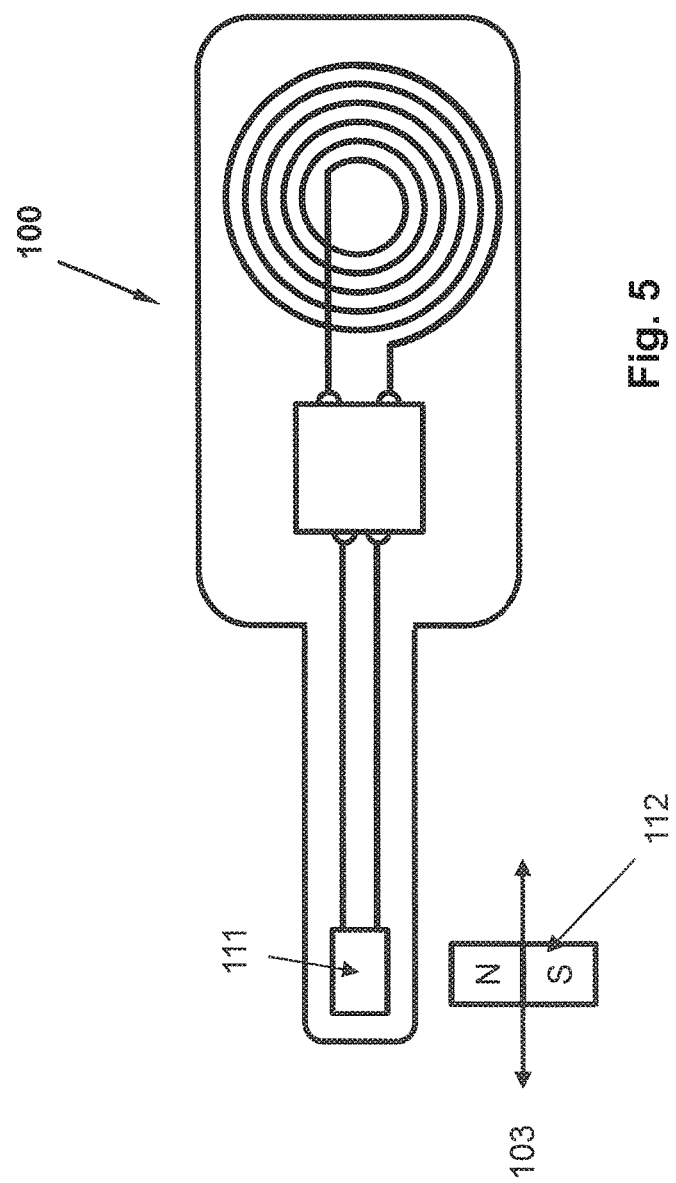
FIG. 5 shows a modification according to the invention of the activatable identifying element in a first and a second state.

FIG. 5 shows another modification of the activatable identifying element 100 according to the invention, wherein here a first receiver with a first pickup 111 on the carrier 108 and with a corresponding transmitter 112 on the second device part 103 preferably has a magnet or paramagnetic element, an electrical, inductive or electromagnetic source, a reflector, a damping element or an optical fiber or refractor, for example, whereby the corresponding field coupling or operative connection between pickup 111 and transmitter 112 is measurably changed by the movement of the first device part 102 relative to the second device part 103.

FIGS. 6*a* and 6*b* show an additional modification of the activatable identifying element according to the invention in a first and second state, wherein preferably a galvanic connection by means of contacts 113 with corresponding mating contacts, preferably on a conductor 114, are opened or closed as a function of the movement of a first device part 102 relative to a second device part 103.

FIGS. 7*a* and 7*b* show an additional modification of the activatable identifying element according to the invention in a first and a second state, wherein contacts 113 preferably sense a conductor having a resistive coating, whereby a variable resistance value results, which is a function of the position of the first device part 102 relative to the second device part 103.

Figure 2:
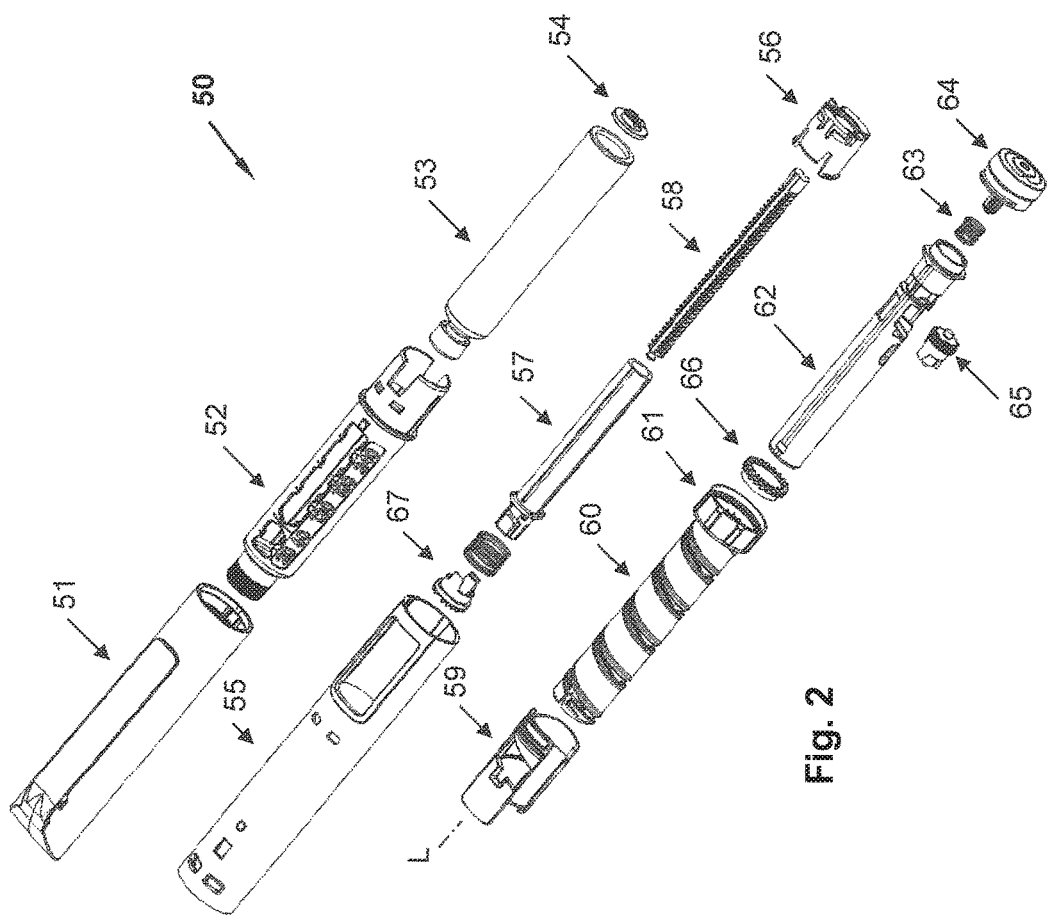
FIG. 2 illustrates, on the example of a pen injector, the device parts on which the invention can be performed, with an activatable identifying element.

FIG. 2 illustrates, on the example of an pen injector, the device parts on which the invention can be performed with an activatable identifying element. In principle, the invention can be performed on all device parts of the pen injector or of a comparable administration device that can assume differentiable positions and characterize significant statuses, in particular before, during or after use. According to the invention, at least two of the individual parts described below can be the respective first and second device part of the autoinjector shown in each case, so long as they move relatively to one another and thereby establish a change of the usage state:

In a first phase during preparation of the autoinjector for use by opening, the protective cap 51 preferably moves relative to the housing 55 having a longitudinal axis L and/or relative to parts fixed to the housing, in particular carpule holder 52, carpule 53, threaded insert 59, or mechanism holder 56. A needle having a hollow cannula (not shown) can be placed on the distal end of the carpule holder 52. A dosage to be administered can be increased or corrected in a second phase by rotating the metering ring 61, whereby the drive sleeve 60 screws out of or into the housing 55 by means of the threaded insert 59. The freely rotatable button 64 is not pressed during this second phase and the coupling ring 66 therefore is loosely situated between the drive sleeve 60 and the coupling sleeve 62, whereby the coupling sleeve 62 is not co-rotated. In a third phase, medicine is discharged by pressing a button 64 by applying an axial force in the distal direction, whereby the coupling ring 66 is pressed on both sides with a frictional engagement between the drive sleeve 60 and the coupling sleeve 62, and the drive sleeve 60 screws back into the housing 55 due to the threaded insert 59. Due to the frictional connection, the coupling sleeve 62 is co-rotated and simultaneously moved distally along the axis L. The coupling sleeve 62, for its part, rotates the axially fixed output drive sleeve 57 by means of a sliding guide. The piston rod 58 is moved distally because of an engagement with a longitudinal guide and by threaded engagement with the output drive sleeve 57 and the housing 55, whereby the flange 54 presses against the piston (not shown) of the carpule 53 and medicine is displaced through the hollow needle.

FIG. 8*a* shows an administration device according to the invention in a first state with an activatable identifying element 100 having the carrier 108, wherein the carrier 108 mechanically accommodates the RFID circuit 106, the antenna 107 and the pickup 104, 105, and connects them electrically to the antenna terminal 106*b* and the signal terminal 106*a*. As shown, a region or portion or pickup part 105 is operatively connected to the first device part 120 and another region or portion or pickup part 104 is operatively connected to the second device part 130.

FIG. 8*b* shows the administration device according to the invention in a second state, wherein the integrity of the carrier, or the pickup 104, 105, has been disrupted by the movement of the first device part 120 relative to the second device by 130, and the above-mentioned operative connection has been disrupted, in particular, the illustrated conductor or conductor loop 104 has been permanently interrupted mechanically and electrically at a separation point 109 in the third state, as can be seen in FIG. 8*c*.

What is claimed is:

1. An administration device for a medicine comprising:
a first device part,
at least one second device part movable relative to the first device part from a first state into at least one second state before or during or after an administration,
and an activatable identifying element comprising:
a carrier,
an RFID circuit with an antenna terminal and at least one signal terminal,
at least one pickup having at least two operatively connected pickup parts, of which at least one pickup part is connected to the at least one signal terminal,
and an antenna that is connected to the antenna terminal,
wherein the carrier receives or connects the RFID circuit, the antenna and the at least one pickup part and
at least one region or portion of the carrier is connected to at least the first device part and has the at least one pickup part, and the second pickup part is connected to the at least one second device part and wherein a movement of the at least one second device part relative to the first device part from the first to the at least one second state effects a signal change of the at least one pickup.

2. An administration device according to claim 1, wherein the operative connection between the two pickup parts is established galvanically or via a magnetic or electrical or electromagnetic field, and wherein the at least one pickup has respective corresponding contacts and mating contacts or respective corresponding detectors and transmitters.

3. An administration device according to claim 1, wherein the first and the second device parts each comprise one of: housing, protective cap, protective means, design shell, grip shell, mechanism holder, packaging, sleeve, blister film, needle adapter, needle, hollow cannula, carpule or syringe holder, cap, needle protection sleeve, pull tab, carpule, septum, syringe, piston, flange, piston rod, plunger, metering sleeve, metering ring drive element, drive spring, motive spring, scale element, counter, locking element, drive spring, drive motor, ratchet, click element, catch arm, blocking element, holding arm, guide, trigger element, trigger, coupling, button, thread, gear unit, or stop.

4. An administration device according to claim 1, wherein the device is an autoinjector, injection pen, autopen, infusion pump, patch pump, inhaler or bolus injector.

5. An administration device according to claim 1, wherein the carrier is two-dimensional, can carry readable information, and is applied at least in part to the outer surface of the administration device or to a surface of the administration device that is visible from outside.

6. An administration device according to claim 1, wherein the carrier is attached with a form fit or frictional fit to at least the first device part and at least in part in an interior of the administration device.

7. An administration device according to claim 6, wherein the carrier is attached in an annular gap formed between device parts.

8. An administration device according to claim 1, wherein the RFID circuit provides codes distinguishable by a read-out device, which are a function of a signal that is present at the at least one signal terminal.

9. An administration device according to claim 1, wherein the RFID circuit is compatible with devices and systems that operate according to a near field communication (NFC) protocol.

10. An administration device according to claim 1, wherein the at least one region or portion of the carrier also receives the second pickup part and is thus connected to the at least one second device part such that a movement of the at least one second device part relative to the first device part from a first into a second state deforms or separates the at least one region or portion of the carrier mechanically.

11. An administration device according to claim 10, wherein the deformation or separation of the at least one region or portion of the carrier influences the operative connection of the at least two pickup parts and effects a signal change of the at least one pickup.

12. An administration device according to claim 11, wherein the at least one pickup has a separable conductor or a variable resistor or a piezoelectric transducer for effecting the signal change.

13. A method performed with an administration device for a medicine, comprising the following steps:
providing in the administration device a first device part, at least one second device part movable relative to the first device part from a first state into at least one second state before or during or after an administration, and an activatable identifying element comprising:
a carrier,
an RFID circuit with an antenna terminal and at least one signal terminal, at least one pickup having at least two operatively connected pickup parts, of which at least one pickup part is connected to the at least one signal terminal, and an antenna that is connected to the antenna terminal;

wherein the carrier receives or connects the RFID circuit, the antenna and the at least one pickup part and at least one region or portion of the carrier is connected to at least the first device part and has the at least one pickup part, and the second pickup part is connected to the at least one second device part and wherein a movement of the at least one second device part relative to the first device part from the first to the at least one second state effects a signal change of the at least one pickup; and with a read out device, reading a first code signaled from the RFID circuit, if the second device part is in the first state; or reading a second code distinguishable from the first code signaled from the RFID circuit if the second device part is in the second state.

14. A method according to claim 13, further comprising at least one of the following steps:

outputting a message depending on the code read, linking the code read or a message to a time stamp, storing a code read or a message in the read-out device or a network-attached storage site, a database or cloud storage, comparing a code read or a message to one or more specified values and outputting a corresponding confirmation or warning, transmitting a code read or a message to a host system or a network or a database or a remote control unit or a blood sugar measuring device or a telemedicine system, or querying databases and outputting corresponding responses.

15. A method according to claim 14 wherein in the case of outputting a message, the message takes the form of one or more of a text or image on a display or a video or audio message or an URL.

16. A method according to claim 14 wherein the read out device provides a code that is communicated to a system that uses the code to assess compliance with a therapy associated with a patient associated with the administration device.

17. A method performed with an administration device for a medicine, the device comprising:

a first device part, at least one second device part movable relative to the first device part from a first state into at least one second state before or during or after an administration, and an activatable identifying element comprising:

an RFID circuit with an antenna terminal and at least one signal terminal, at least one pickup having at least two operatively connected pickup parts, of which at least one pickup part is connected to the at least one signal terminal, and an antenna that is connected to the antenna terminal;

the method comprising the following steps:

controlling a read out device to supply energy temporarily to the RFID circuit;

reading a code signaled from the RFID circuit, that indicates whether the second device part is in the first state; or the second device part is in the second state; and using the code to assess compliance with a therapy associated with a service provider using the administration device.

18. An administration device for a medicine comprising:

a first device part, at least one second device part movable relative to the first device part from a first state into at least one second state before or during or after an administration, and an activatable element for transmitting information comprising:

a carrier, an RFID circuit with an antenna terminal and at least one signal terminal, at least one pickup having at least two operatively connected pickup parts, of which at least one pickup part is connected to the at least one signal terminal, and an antenna that is connected to the antenna terminal, wherein the carrier receives or connects the RFID circuit, the antenna and the at least one pickup part and at least one region or portion of the carrier is connected to at least the first device part, whereby relative motion of the first device part and at least one second device part establishes a change of usage state signal detectable at the at least one signal terminal of the device and transmittable from the activatable element.

19. An administration device according to claim 18, wherein the relative motion of the first device part and at least one second device part effects deformation or separation of the at least one region or portion of the carrier or other change detectable by an active or passive sensor associated with the at least one pickup.

* * * * *